US 5,837,260

US005837260A

United States Patent [19]
Cohen et al.
[11] Patent Number: 5,837,260
[45] Date of Patent: Nov. 17, 1998
[54] CHIMERIC HEPATITIS A VACCINE

[75] Inventors: Jeffrey I. Cohen, Brighton, Mass.; Robert H. Purcell, Boyds, Md.; Stephen M. Feinstone, Washington, D.C.; John R. Ticehurst, Bethesda, Md.

[73] Assignee: The United of America as represented by the Department of Health and Human Services, Washington, D.C.

[21] Appl. No.: 473,304

[22] Filed: Jun. 7, 1995

Related U.S. Application Data

[62] Division of Ser. No. 120,646, Sep. 13, 1993, Pat. No. 5,478,746, which is a continuation of Ser. No. 789,640, Nov. 12, 1991, abandoned, which is a continuation of Ser. No. 462,915, Jan. 12, 1990, abandoned, which is a continuation of Ser. No. 462,915, Jan. 12, 1990, abandoned, which is a continuation of Ser. No. 88,220, Aug. 24, 1987, abandoned, which is a continuation-in-part of Ser. No. 905,146, Sep. 9, 1986, abandoned, which is a continuation-in-part of Ser. No. 652,067, Sep. 19, 1984, Pat. No. 4,620,978, which is a continuation-in-part of Ser. No. 366,165, Apr. 7, 1982, Pat. No. 4,532,215.

[51] Int. Cl.[6] .......................... A61K 39/29; A61K 39/12; C12N 7/00; C12N 7/04

[52] U.S. Cl. .................................... 424/226.1; 424/204.1; 424/205.1; 424/225.1; 435/235.1; 435/236.1; 435/237; 435/320; 536/23.1

[58] Field of Search ............................. 435/320.1, 235.1, 435/236, 237, 238; 424/204.1, 205.1, 226.1, 225.1; 536/23.1

[56] References Cited

U.S. PATENT DOCUMENTS 4,164,566 8/1979 Provost et al. ............................ 424/89

5,021,348 6/1991 Gieba et al. ............................ 435/237

OTHER PUBLICATIONS

Ticehurst, et al., (1983) *Proc. Natl. Acad. Sci. USA* 80:5885–5889.

Cohen, et al., (1987) *Journal of Virology* 61:50–59.

Cohen, et al., (1987) *Proc. Natl. Acad. Sci. USA*, 84:2497–2501.

Provost et al. (A) Proc. Soc. Exp. Bio. Med., 170:8–14, 1982.

Provost et al. (B) Proc. Soc. Exp. Bio. Med., 172:357–363, 1983.

Fienstone et al., Develop. Biol. Stano., 54:429–432, 1983.

Ticehurst et al., PNAS USA, 80:5885–5889, Oct. 1983.

Provost et al. (D) Proc. Soc. Exp. Bio. Med., 159:201–203, 1978.

*Primary Examiner*—Marian C. Knode
*Assistant Examiner*—Jay Williams
*Attorney, Agent, or Firm*—Morgan & Finnegan, L.L.P.

[57] ABSTRACT

A full-length cDNA copy of an attenuated, cell culture-adapted hepatitis-A virus genome has been constructed. The HAV cDNA when inserted, without the oligo (dG) oligo (dC) tails, into an RNA transcription vector yielded a plasmid designated pHAV/7. Transfection of monkey kidney cells with pHAV/7 DNA yielded HAV. Transfection with RNA transcripts produced in vitro from pHAV/7 yielded about 10-fold more HAV than transfection with pHAV/7 DNA. HAV thus produced are useful as a vaccine.

6 Claims, 2 Drawing Sheets

CHIMERIC HEPATITIS A VACCINE

This is a divisional of application Ser. No. 08/120,646 filed Sep. 13, 1993 now U.S. Pat. No. 5,478,746, which is a continuation of application Ser. No. 07/789,640, filed Nov. 12, 1991, abandoned, which is a continuation of application Ser. No. 07/462,915 filed Jan. 12, 1990, abandoned, which is a continuation of application Ser. No. 07/088,220, filed Aug. 24, 1987, abandoned, which is a continuation-in-part of application Ser. No. 06/905,146, filed Sep. 9, 1986, abandoned, which is a continuation-in-part of application Ser. No. 06/652,067, filed Sep. 19, 1984, now U.S. Pat. No. 4,620,978, issued Nov. 4, 1986, which is a continuation-in-part of application Ser. No. 06/366,165, filed Apr. 7, 1982, now U.S. Pat. No. 4,532,215, issued Jul. 30, 1985.

BACKGROUND OF THE INVENTION

The present invention is related to hepatitis vaccines. More particularly, the present invention is related to producing live or killed virus vaccines employing full-length, hepatitis-A virus cDNA or RNA transcribed therefrom as the transfecting agent. The cDNA can be specifically mutated to produce a hepatitis-A virus with the desired vaccine characteristics.

STATE OF THE ART

Heretofore live vaccines have been produced by the conventional method of producing attenuated virus by passaging wild type virus in cell culture. This is an empirical process which depends on random natural mutation. Randomness of the mutational process makes it difficult to predict and obtain viruses which are infectious yet sufficiently attenuated so as to be suitable as a vaccine (*J. Med. Virol.* 20:165–175, 1986). The present invention overcomes such limitations of the conventional methodology and provides a new approach to vaccine preparation.

SUMMARY OF THE INVENTION

It is, therefore, an object of the present invention to provide a method for specific mutations to be placed into the wild type or attenuated viral genome in a deliberate manner to produce candidate vaccine viruses or viruses with other desirable characteristics such as high titer growth in cell culture which would allow for the preparation of killed virus vaccine.

It is a further object of the present invention to provide a full-length DNA analog of hepatitis-A virus genome or RNA transcripts thereof which can encode infectious hepatitis-A virus in a suitable host cell or expression vector.

It is yet another object of the present invention to provide a genetically stable repository for a live hepatitis-A vaccine or a substrate which could be purposefully mutated to yield candidate hepatitis A vaccine viruses.

Other objects and advantages will become evident from the Detailed Description of the Invention.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Hepatitis A virus (HAV) is a positive-strand RNA virus which is a member of the picornavirus family. The genome of wild-type HAV strain HM-175 is 7,478 nucleotides long, followed by a poly (A) tail, and encodes a polyprotein of 2,227 amino acids (Cohen et al, *J. Virol.* 61:50–59, 1987). Wild-type HAV grows poorly in cell culture, is not cytopathic, and produces low yields of virus. Although HAV RNA (extracted from virions) is infectious in cell culture (Locarnini et al, *J. Virol.* 37:216–225, 1981 and Siegl et al, *J. Gen. Virol.* 57:331–341, 1981), direct manipulation of the viral genome (such as analysis of specific mutants and recombinants) becomes difficult because of its RNA composition. However, such manipulations would be useful to study areas of the genome responsible for cell culture-adaptation, viral attenuation and virulence and specific viral functions.

Recently the nucleotide sequence of cDNA from an attenuated, cell culture-adapted HAV has been determined (Cohen et al, *Proc. Natl. Acad. Sci USA* 84:2497–2501, 1987). This virus is attenuated for chimpanzees, partially attenuated for marmosets but has not yet been tested in humans. Described herein is the assembly of cDNA clones from this virus to form a full-length cDNA copy of the genome. In addition, RNA transcripts were produced in vitro from this cDNA. Tests were then conducted with cultured mammalian cells by transfecting them with the HAV cDNA or RNA transcripts to produce infectious HAV which could be used as vaccines.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

MATERIALS AND METHODS

Construction of full-length HAV cDNA

Figure 1:
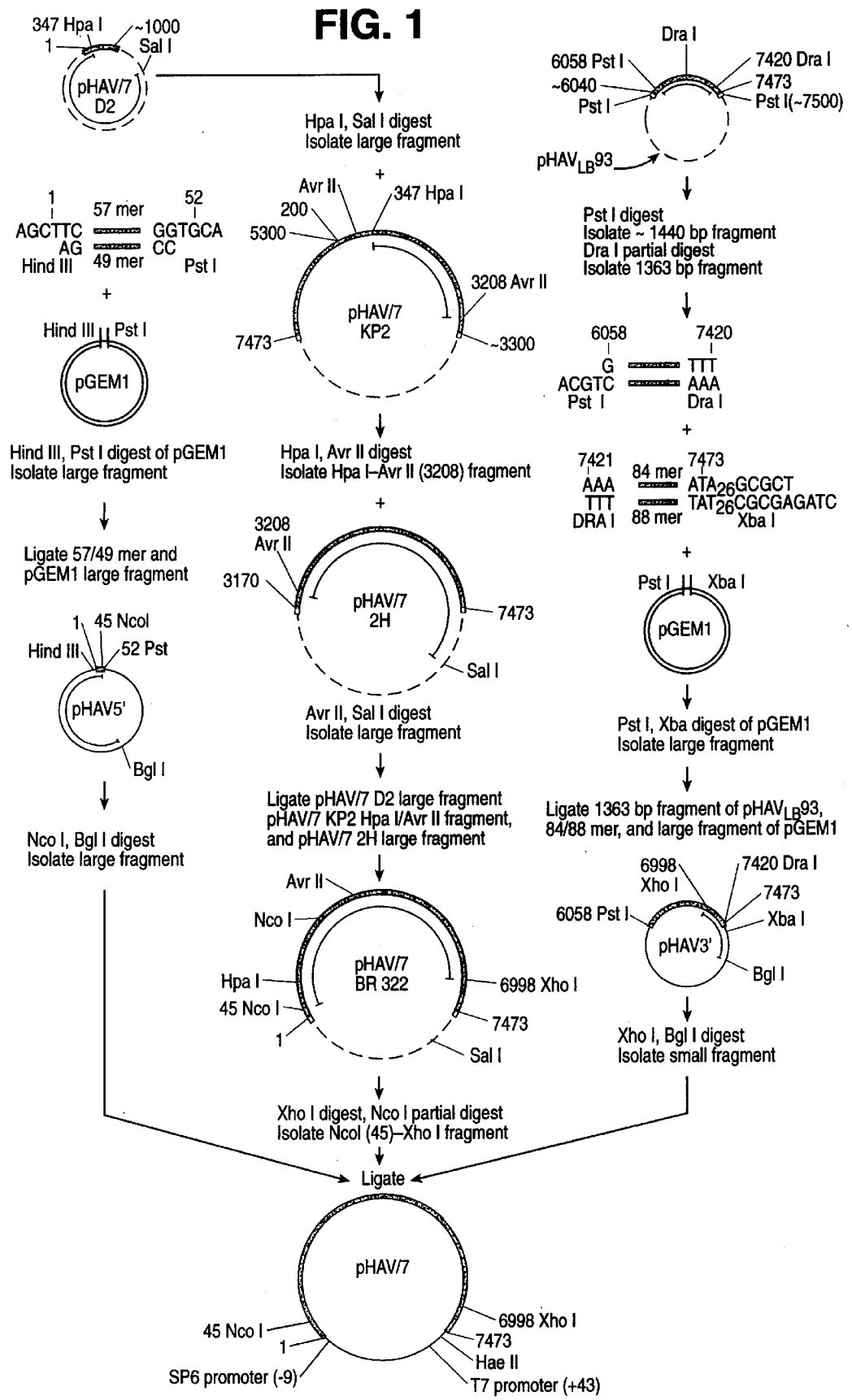
FIG. 1 schematically illustrates construction of full-length HAV HM-175/7 MK-5 cDNA in pGEM1. Single lines indicate pGEM1 DNA, dashed lines indicate pBR322 DNA, solid bars indicate HAV cDNA, open bars indicate oligo (dG) oligo (dC) tails on ends of cDNA. Numbers refer to nucleotides of HAV HM-175/7 MK-5 RNA, numbers in parentheses refer to nucleotides of pGEM1. Column 1 shows construction of 5' end of HAV cDNA in pGEM1, column 2 shows construction of full-length HAV cDNA in pBR322, column 3 shows construction of 3' end of HAV cDNA in pGEM1. Plasmid HAV/7 KP2 contains two discontinuous portions of the HAV genome arranged head-to-head. pHAV$_{LB}$93 is a cDNA clone from wild-type HAV HM-175 however, nucleotide positions have been renumbered (5 bases deleted) to correspond to HAV HM-175/7 MK-5.
Figure 2:
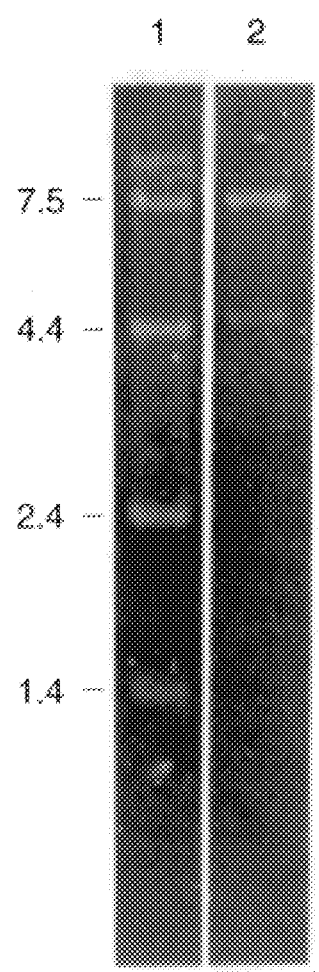
FIG. 2 shows RNA transcribed from pHAV/7 using SP6 polymerase. RNA was denatured with 50% formamide and 6.4% formaldehyde and electrophoresed on a 1% agarose gel containing 2% formaldehyde. Lane 1 indicates RNA size markers and lane 2 indicates plus-strand RNA. Each marker band contains 0.67 µg of RNA; RNA in lane 2 represents 2% of the SP6 polymerase reaction.

Molecular cloning of HAV HM-175/7 MK-5 was achieved as described by Cohen et al, supra. A set of three cDNA clones, pHAV/7 D2, pHAV/7 KP2, and pHAV/7 2H, span the entire genome of the virus. Restriction endonuclease fragments from these three clones were ligated together (FIG. 1, Column 2) and the resulting plasmid, pHAV/7 BR322, contained a full-length cDNA copy of HAV HM-175/7 MK-5 in plasmid vector pBR322. The HAV cDNA insert in this plasmid is bracketed by oligo (dG) oligo (dC) tails remaining from the cloning procedure.

In order to contruct full-length HAV cDNA without oligo (dG) oligo (dC) tails, double-stranded oligonucleotides were synthesized representing the 5' and 3' termini of the viral genome. Two oligonucleotides (57 mer, 49 mer) were synthesized (Applied Biosystems 380A DNA Synthesizer, Foster City, Calif.) corresponding to the 5' end of wild-type HAV HM-175 virion RNA (and its complementary strand) with Hind III and Pst I restriction sites at the 5' and 3' ends, respectively (FIG. 1, Column 1). After gel purification and annealing of the complementary oligonucleotides, the resultant double-stranded DNA was ligated to plasmid vector pGEM1 (Promega Biotec, Madison, Wis.) to yield pHAV5'.

Similarly, two oligonucleotides (84 mer, 88 mer) were synthesized corresponding to the 3' end of the wild-type HAV HM-175 RNA (and its complementary strand) with a 26 base oligo (dA) oligo (dT) tail, followed by Hae II and Xba I restriction sites (FIG. 1, Column 3). After gel purification and annealing the resultant DNA was ligated to a restriction fragment from $pHAV_{LB}93$ (a cDNA clone from wild-type HAV HM-175) and pGEM1 to yield pHAV3'.

The appropriate restriction fragments from pHAV5', pHAV/7 BR322, and pHAV3' were ligated together to yield plasmid pHAV/7. This plasmid contains a full-length cDNA copy of HAV HM-175/7 MK-5 in pGEM1 , except for two nucleotide changes. Nucleotides at positions 7027 and 7425 correspond to those of wild-type HAV HM-175 (Cohen et al, supra). The nucleotide sequence at the ligation junctions was determined directly from plasmid DNA using the method of Zagursky et al (*Gene Analysis Techniques* 2:89–94, 1985). All constructs had the expected junction sites.

A deposit of the cDNA clone of the present invention (pMK5) has been made at the ATCC, Rockville, Md. on Aug. 7, 1987, under the accession number 67495. The deposit shall be viably maintained, replacing if it became non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

In Vitro Transcription

Plasmid pHAV/7 was digested with Hae II (cuts immediately after poly [A] tail) and the resultant linear DNA was extracted with phenol/chloroform, and precipitated with ethanol. RNA transcription was performed using SP6 polymerase (Promega Biotec) in a reaction containing 40 mM Tris-HCl pH 7.5, 6 mM $MgCl_2$, 2 mM spermidine-HCl, 10mM NaCl, 10 mM dithiothreitol, RNasin (Promega Biotec), 2$\mu$g of linearized pHAV/7 and 0.5 mM each ATP, CTP, UTP, and GTP. The reaction was incubated at 37° C. for 1 hour, DNase I (0.02 U/ml [RQ-1™, Promega Biotec]) was added, and incubation was continued at 37° C. for 15 minutes. The reaction mixture was extracted with phenol/ chloroform, chloroform, and then precipitated twice with ethanol.

Synthesis of minus-strand RNA was identical to that described above, except that pHAV/7 was linearized with Nar I (cuts 293 bases before 5' end of HAV) and transcription was performed with T7 polymerase.

Transfection of Cells and Detection of HAV

RNA transfections were performed in African green monkey kidney (AGMK) cells (second passage) or CV-1 cells by a modification of the procedure of van der Werf et al (*Proc. Natl. Acad. Sci USA* 83:-2330–2334, 1986). About 4 $\mu$g of RNA (one-half of the transcription reaction product) was dissolved in 0.5 ml HBSS buffer (21 mM Hepes, 137 mM NaCl, 5 mM KCl, 0.7 mM $Na_2HPO_4$, 6 mM dextrose, pH 7.05) and 0.5 ml DEAE-dextran (1 mg/ml in HBSS) was added. AGMK cells in 6 cm dishes (80% confluent) were washed once with Dulbecco's modified Eagle medium (DMEM), 1 ml of RNA in DEAE-dextran was added, and the cells were placed at room temperature (about 22° C. to 25° C.) for 30 minutes. Two ml of DMEM supplemented with 10% (vol/vol) fetal calf serum was added and the cells were incubated at 35° C. for 6 hours with rocking every hour. After 6 hours the medium was removed, the cells were washed twice with DMEM, DMEM supplemented with 10% (vol/vol) fetal calf serum was added, and the cells were incubated at 35° C. DNA transfections were performed as described by Racaniello and Baltimore (*Science* 214:916–919, 1981), except that 5 $\mu$g of plasmid DNA was used for each 6 cm dish and the glycerol shock was performed for 1 minute at room temperature (about 22° C. to 25° C.).

Two weeks after transfection the cells were trypsinized and plated onto glass coverslips. Cells were assayed by fluorescein-labeled antibody (Mathiesen et al, *Infect. Immun.* 18:524–530, 1977) for the production of hepatitis-A antigen each week thereafter.

Animal Studies

Five weeks after transfection, AGMK cells were lysed, pelleted, and 1 ml of DMEM supplemented with 10% fetal calf serum was added. A 25% suspension (vol/vol) of AGMK cell lysate in fetal calf serum was injected intravenously into marmosets (*Saguinus mystax*). Animals were monitored weekly for determination of serum isocitrate dehydrogenase (ICD) and anti-HAV antibody (HAVAB, Abbott Labortatories, Chicago). Serum ICD levels that rose to twice the mean preinoculation value for each animal were considered elevated, if they occurred within four weeks preceding or following seroconversion.

Analysis of RNA Transcripts

RNA produced in vitro from pHAV/7 corresponds to virion RNA except for (a) absence of VPg at the 5' terminus, (b) 10 additional nucleotides at the 5' end (GAATACAAGC), (c) two nucleotide changes corresponding to wild-type HAV HM-175 RNA, and (d) a shortened (26 base) poly (A) tail. Virion RNA contains a 40 to 80 base poly (A) tail. RNA from the transcription reaction was denatured with formamide and formaldehyde (Davis et al, *Basic Methods in Molecular Biology* Elsevier Science Publishing CO., New York P 143–145, 1986) and analyzed on a 1% agarose gel (FIG. 2). The predominant RNA species was 7.5 kb in length, but two additional bands (4.6 kb, 1.6 kb) were noted. Two additional bands (5.5 kb, 3.0 kb) were also noted when minus-strand RNA was synthesized using T7 polymerase. It has been reported that when poliovirus cDNA was transcribed using SP6 or T7 polymerase, an additional band attributed to premature transcription termination was seen (Kaplan et al, *Proc. Natl. Acad. Sci. USA* 82:8424–8428, 1985).

DNA and RNA transfections

Three weeks after transfection with RNA transcripts from HAV/7 about 10% of AGMK cells were found to be producing hepatitis-A antigen (Table 1). By five weeks after transfection about 80 of the cells were producing antigen. It is noted that RNA transcripts treated with RNase A before transfection, and minus-strand RNA transcripts did not yield hepatitis-A antigen.

TABLE 1

Transfection of monkey kidney cells with HAV cDNA and its RNA transcripts.

| Nucleic Acid | HAV Produced |
|---|---|
| Secondary African green monkey kidney cells | |
| RNA DEAE-dextran | |
| pHAV/7 + DNase I | + |
| pHAV/7 + DNase I + RNase A | − |
| pHAV/7 minus-strand + DNase I | − |
| DNA Calcium-phosphate | |
| pHAV/7 | + |
| pHAV/7 + RNase A | + |
| pHAV/7 + DNase I | − |
| pHAV/7 BR322 | − |
| CV-1 Cells | |
| RNA DEAE-dextran | |
| pHAV/7 + DNase I | + |
| pHAV/7 + DNase I + RNase | − |

Three weeks after transfection with pHAV/7 DN, about 1% of AGMK cells were producing hepatitis-A antigen. Transfection with pHAV/7 DNA treated with RNase A also yielded antigen; however, transfection with pHAV/7 BR332 DNA or pHAV/7 treated with DNase I failed to yield antigen.

Five weeks after transfection, AGMK cells that had received RNA transcripts from pHAV/7 were trypsinized, pelleted, and resuspended in 1.0 ml of DMEM supplemented with 10% (vol/vol) fetal calf serum. The cells were then frozen, thawed, sonicated three times, and inoculated onto uninfected BS-C-1 cells. One week later, hepatitis-A antigen was detected in BS-C-1 cells. The original AGMK cell lysate contained about $10^{7.8}$ 50% tissue culture infectious doses ($TCID_{50}$) per ml. Hepatitis-A antigen was not detected in BS-C-1 cells inoculated with cell cultures from the control transfections.

Marmosets inoculated intravenously with 0.125 ml of AGMK cell suspension ($10^{6.9}$ $TCID_{50}$) developed anti-HAV antibodies within six weeks of inoculation (Table 2). The geometric mean peak ICD was 2252 sigma units/ml (2.99× the mean preinoculation value). Marmosets inoculated with AGMK cell lysate obtained after transfection with an earlier HAV construct (which failed to yield detectable virus in vitro) did not develop anti-HAV antibody (data not shown).

TABLE 2

Liver enzymes of marmosets receiving virus recovered from transfection.

| Marmoset Number | Mean Preinoculation ICD[+] | Peak ICD[+] | Week after inoculation until Peak ICD[+] | Positive HAVAB |
|---|---|---|---|---|
| 457 | 1047 | 1903 | 8 | 4 |
| 458 | 668 | 4038 | 8 | 4 |
| 475 | 766 | 1167 | 3 | 5 |
| 476 | 621 | 2798 | 5 | 6 |

[+]ICD in sigma units/ml
HAVAB = HAV Antibody

Preparation of HAV Vaccine for Human Use

The development of infectious hepatitis-A virus cDNA and RNA transcripts thereof provides a substrate for a hepatitis-A vaccine. The hepatitis-A virus cDNA can now be purposefully mutated to produce a virus with one or more of several desirable properties for vaccine production:

(a) attenuation such that no disease is produced in man but the virus replicates and induces protective antibody;

(b) better growth in cell culture such that large quantities of virus are obtained inexpensively so that a practical inactivated vaccine is produced; and (c) changes in the viral antigen which could result in higher antibody production.

The hepatitis-A virus cDNA can be purposefully mutated in one or more of several ways. First, site directed mutagenesis can be used to add, delete or change one or more nucleotides (Zoller et al, DNA, 3: 479–488, 1984). In this procedure an oligonucleotide is synthesized containing the appropriate mutation and annealed to a portion of single stranded HAV cDNA. The resulting hybrid molecule is used for transforming bacteria and double-stranded DNA is then isolated containing the desired mutation. This double-stranded DNA is then used to produce full-length cDNA (by ligation to a restriction fragment of the latter) which is then transfected into cell culture. The resulting virus then has the desired mutation. Alternatively, two oligonucleotides can be synthesized which contain the desired mutation. These may then be annealed to form double-stranded DNA that can be inserted in the hepatitis-A cDNA to produce full-length cDNA.

Also, a portion of cDNA from another virus (e.g. attenuated poliovirus or another hepatitis-A virus) might be inserted into the hepatitis-A cDNA and the resultant cDNA may share the attenuated phenotype (or other desired property) of the donor virus. Additionally, a portion of the hepatitis-A cDNA could be randomly mutated by chemical, ionizing radiation, or other techniques. This DNA may then be used to produce full-length hepatitis-A cDNA (by the method described above) which could be used to produce mutant virus. Those skilled in the art will know that additional mutagenesis schemes are currently available and could be employed to produce mutations in hepatitis-A cDNA.

In summary, it is clear from the above that transfection of AGMK cells with HAV cDNA and RNA transcripts from HAV cDNA yields HAV. However, transfection with RNA transcripts of HAV cDNA is more efficient than with HAV cDNA as evidenced by the earlier production of virus and the higher percentage of cells infected. Marmosets receiving virus recovered from transfection had a mean peak ICD of 2252 sigma units/ml. Two of the four animals had ICD elevations greater than twice their preinoculation value. Marmosets that received HAV HM-175/7 MK-2 (three cell culture passages earlier than the virus used for cDNA cloning in this study) had a mean peak ICD of 1686 sigma units/ml and two out of five animals had ICD elevations greater that twice their preinoculation value. In contrast, marmosets that received wild-type HAV-HM-175 had a mean peak ICD of 6076 sigma units/ml and all (four of four) had ICD elevations greater than twice the preinoculation value.

Thus, marmosets inoculated with transfection-derived virus developed liver enzyme elevations more closely resembling the enzyme elevations seen in animals inoculated with virus from a comparable level of cell culture passage than wild-type virus. These results demonstrate that the phenotype for attenuation was retained by the molecularly cloned virus.

Availability of the infectious RNA transcripts of HAV cDNA of the present invention now makes it feasible to further study the biology of HAV. For instance, the chimeric HAVs derived from recombinants of wild-type and attenuated (cell culture-adapted) infectious cDNAs (or RNAs) of the present invention can be employed for mapping areas of the genome responsible for attenuation and cell culture adaptation. Chimeric viruses can also be produced from recombinants of HAV and other picornaviruses. Moreover, site-directed in vitro mutagenesis of HAV cDNA now becomes possible for the first time because of the availability of the full-length HAV cDNA of the present invention, such mutagenesis being quite useful in producing desirable HAV viruses with new phenotypes.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An attenuated, cell-culture adapted, infectious hepatitis A virus of the HM-175 strain produced by cells containing a nucleic acid molecule which has a nucleic acid sequence corresponding to the sequence of HAV HM-175/7 MK-5 except for the nucleotides at positions 7027 and 7425 which are those of wild-type hepatitis A virus HM-175.

2. An attenuated, cell-culture adapted, infectious hepatitis A virus produced by cells containing a nucleic acid molecule contained in an expression vector having ATCC deposit number 67495.

3. A killed hepatitis A vaccine comprising the hepatitis A virus of claim 1.

4. A killed hepatitis A vaccine comprising the hepatitis A virus of claim 2.

5. A live hepatitis A vaccine comprising the hepatitis A virus of claim 1.

6. A live hepatitis A vaccine comprising the hepatitis A virus of claim 2.

* * * * *